United States Patent [19]
Adolphi et al.

[11] 3,932,632
[45] Jan. 13, 1976

[54] INSECTICIDAL COMPOSITIONS CONTAINING AN ORGANOPHOSPHORUS COMPOUND AND A THIOLCARBAMATE

[75] Inventors: Heinrich Adolphi, Limburgerhof; Hans-Dieter Hoffmann, Ludwigshafen; Karl-Heinz Koenig, Frankenthal; Wolfgang Rohr, Mannheim, all of Germany

[73] Assignee: Badische Anilin- & Soda-Fabrik Aktiengesellschaft, Ludwigshafen, Germany

[22] Filed: Aug. 15, 1973

[21] Appl. No.: 388,427

[30] Foreign Application Priority Data
Sept. 8, 1972   Germany............................ 2244090

[52] U.S. Cl................................. 424/213; 424/300
[51] Int. Cl.² ...................... A01N 9/12; A01N 9/36

[58] Field of Search............................ 424/213, 300

[56] References Cited
UNITED STATES PATENTS

| | | | |
|---|---|---|---|
| 2,990,316 | 6/1961 | Jones et al. | 424/213 |
| 2,990,319 | 6/1961 | Jones et al. | 424/213 |

OTHER PUBLICATIONS
Chemical Abstracts 61: 5567h (1964).

*Primary Examiner*—Leonard Schenkman
*Attorney, Agent, or Firm*—Johnston, Keil, Thompson & Shurtleff

[57] ABSTRACT

New and valuable pesticide on the basis of an active ingredient from the group of organophosphorus compounds or chlorinated hydrocarbons, and additionally containing a thiol carbamate.

4 Claims, No Drawings

INSECTICIDAL COMPOSITIONS CONTAINING AN ORGANOPHOSPHORUS COMPOUND AND A THIOLCARBAMATE

It is well known to control animal pests with chemical active ingredients, the aim being to prevent damage to crops, to protect stores or materials, to destroy disease vectors and so on.

In many cases, however, certain pest strains have developed increased or total resistance to conventional active ingredients. These resistant strains are particularly well-known in the case of insects, mites and ticks, and are a serious problem.

There is therefore a considerable interest in finding substances capable of partially or completely breaking down an acquired resistance. These substances themselves do not have to have insecticidal or acaricidal properties.

We have now found that pesticides based on organophosphorus compounds or chlorinated hydrocarbons and which additionally contain a thiol carbamate of the formula

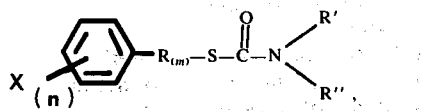

where X denotes alkyl (methyl, ethyl, isopropyl, n-propyl, n-butyl, isobutyl), alkoxy (methoxy, ethoxy, n-propoxy, isopropoxy), halogen (fluoro, chloro, bromo, iodo), $n$ denotes one of the integers 0, 1 and 2, m denotes one of the integers 0 and 1, R denotes one of the radicals $-CH_2-$, $-C_2H_4-$,

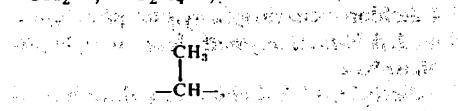

and $-C_3H_6-$, and R' and R'' are identical or different and each denotes alkyl (methyl, ethyl, isopropyl, n-propyl, n-butyl, sec-butyl, isobutyl, tert-butyl, n-pentyl, isopentyl), cycloalkyl (cyclopentyl, cyclohexyl, cycloheptyl, 3-methylcyclohexyl, 4-methylcyclohexyl), alkenyl (allyl, butynyl, methallyl), and alkynyl (propargyl, butynyl, isobutynyl), or R' and R'', together with the nitrogen atom whose substituents they are, denote a saturated heterocyclic ring (tetramethylenimine, pentamethylenimine, hexamethylenimine, heptamethylenimine radical) which may be substituted by one or more alkyl radicals (one to three methyl, ethyl, propyl or isopropyl groups) are effective against pests belonging to strains resistant to organophosphorus compounds and chlorinated hydrocarbons.

Examples of such pests are *Tribolium confusum*, *Tribolium castaneum*, *Blattella germanica*, *Periplaneta americana*, *Musca domestica*, *Aedes aegypti*, *Anopheles maculipennis*, and *Boophilus microplus*.

The pesticides according to the invention may contain the active ingredients and thiol carbamates in widely varying ratios, e.g., a weight ratio of from 10:1 to 1:10 (active ingredient: thio carbamate). The preferred weight ratio is 1:1.

The pesticides according to the invention are employed in conventional manner, e.g., spraying, atomizing or dusting. It is essential that the pesticide comes into contact with the pest. Examples of organophosphorus compounds and chlorinated hydrocarbons are as follows:

bis-O,O-diethylphosphoric anhydride
dimethyl-(2,2,2-trichloro-1-hydroxyethyl)-phosphonate
1,2-dibromo-2,2-dichloroethyldimethyl phosphate
2,2-dichlorovinyldimethyl phosphate
2-methoxycarbamyl-1-methylvinyldimethyl phosphate
dimethyl-1-methyl-2-(methylcarbamoyl)-vinyl phosphate cis
3-(dimethoxyphosphynyloxy)-N,N-dimethyl-cis-crotonamide
2-chloro-2-diethylcarbamoyl-1-methylvinyldimethyl phosphate
O,O-diethyl-O(or S)-2-(ethylthio)-ethyl thiophosphate
S-ethylthioethyl-O,O-dimethyl dithiophosphate
O,O-diethyl-S-ethylmercaptomethyl dithiophosphate
O,O-diethyl-S-2-(ethylthio)-ethyl dithiophosphate
O,O-dimethyl-S-2-(ethylsulfynyl)-ethyl thiophosphate
O,O-dimethyl-S-(1,2-dicarbethoxy)-ethyl dithiophosphate
O,O,O,O-tetraethyl-S,S'-methylene bis-dithiophosphate
O-ethyl-S,S-dipropyl dithiophosphate
O,O-dimethyl-S-(N-methyl-N-formylcarbamoylmethyl)-dithiophosphate
O,O-dimethyl-S-(N-methylcarbamoylmethyl)-dithiophosphate
O,O-dimethyl-O-p-nitrophenyl thiophosphate
O,O-diethyl-O-p-nitrophenyl thiophosphate
O-ethyl-O-p-nitrophenylphenyl thiophosphonate
O,O-dimethyl-O-(4-nitro-m-tolyl)-thiophosphate
O,O-dimethyl-O-2,4,5-trichlorophenyl thiophosphate
O-ethyl-1,2,4,5-trichlorophenylethyl thiophosphonate
O,O-dimethyl-O,2,5-dichloro-4-bromophenyl thiophosphate
O,O-dimethyl-O-(2,5-dichloro-4-iodophenyl)-thiophosphate
4-tert-butyl-2-chlorophenyl-N-methyl-O-methylamido phosphate
O,O-dimethyl-O-(3-methyl-4-methylmercaptophenyl)-thiophosphate
isopropylamino-O-ethyl-O-(4-methylmercapto-3-methylphenyl)-phosphate
O,O-diethyl-O-p-(methylsulfynyl)-phenyl thiophosphate
O-p-(dimethylsulfamido)-phenyl-O,O-dimethyl thiophosphate
O,O,O',O'-tetramethyl-O,O'-thiodi-p-phenylene thiophosphate
O-ethyl-S-phenylethyl dithiophosphonate
O,O-dimethyl-O-(α-methylbenzyl-3-hydroxycrotonyl)-phosphate
2-chloro-1-(2,4-dichlorophenyl)-vinyl-diethylphosphate 2-chloro-1-(2,4,5-trichlorophenyl)-vinyl dimethyl phosphate
O-[2-chloro-1-(2,5-dichlorophenyl)-vinyl]-O,O-diethyl thiophosphate
phenylglyoxylonitrile oxime-O,O-diethyl thiophosphate
O,O-diethyl-O-(3-chloro-4-methyl-2-oxo-2-H-1-benzopyran-7-yl thiophosphate
2,3-p-dioxanedithiol-S,S-bis-(O,O-diethyl dithiophosphate)

5-[(6-chloro-2-oxo-3-benzoxazolynyl)-methyl]-O,O-diethyl dithiophosphate
2-(diethoxyphosphynylimino)-1,3-dithiolane
O,O-dimethyl-S-(2-methoxy-1,3,4-thiadiazol-5-(4H)-onyl-(4) methyl)-dithiophosphate
O,O-dimethyl-S-phthalimidomethyl dithiophosphate
O,O-diethyl-O-(3,5,6-trichloro-2-pyridyl)-thiophosphate
O,O-diethyl-O-2-pyrazinyl thiophosphate
O,O-diethyl-O-(2-isopropyl-4-methyl)-6-pyrimidyl)-thiophosphate
O,O-diethyl-O-(2-quinoxalyl)-thiophosphate
O,O-dimethyl-S-(4-oxo-1,2,3-benzotriazin-3-(4H)-ylmethyl)-dithiophosphate
O,O-diethyl-S-(4-oxo-1,2,3-benzotriazin-3-(4H-ylmethyl)-dithiophosphate
O,O-dimethyl-O-(3-chloro-4-nitrophenyl)-thiophosphate
O,O-dimethyl-O (or S)-2-(ethylthioethyl)-thiophosphate
2-(O,O-dimethylphosphorylthiomethyl)-5-methoxypyrone-3,4-dichlorobenzyltriphenylphosphonium chloride
O,O-diethyl-S-(2,5-dichlorophenylthiomethyl)-dithiophosphate
O,O-diethyl-O-(4-methylcoumarinyl-7)-thiophosphate
5-amino-bis-(dimethylamido)-phosphinyl-3-phenyl-1,2,4-triazole
N-methyl-5-(O,O-dimethylthiophosphoryl)-3-thiavaleramide
O,O-diethyl-O-(2-dimethylamino-4-methylpyrimidyl-(6)-thiophosphate
O,O-dimethyl-S-(methylcarbamoylmethyl)-thiophosphate
O-ethyl-O-(8-quinolinyl)-phenyl thiophosphonate
O-methyl-S-methylamido thiophosphate
O-methyl-O-(2,5-dichloro-4-bromophenyl)-benzothiophosphonate
O,O,O,O-tetrapropyl dithiopyrophosphate
3-(dimethoxyphosphinyloxy)-N-methyl-N-methoxy-cis-crotonamide
O,O-dimethyl-S-(N-ethylcarbamoylmethyl)-dithiophosphate
O,O-diethyl-S-(N-isopropylcarbamoylmethyl)-dithiophosphate
S-N-(1-cyano-1-methylethyl)-carbamoylmethyldiethylthiolphosphate
S-(2-acetamidoethyl)-O,O-dimethyl dithiophosphate
hexamethylphosphoric triamide
O,O-dimethyl-O-(2-chloro-4-nitrophenyl)-thiophosphate
O,O-dimethyl-O-p-cyanophenyl thiophosphate
O-ethyl-O-p-cyanophenyl thiophosphonate
O,O-diethyl-O,2,4-dichlorophenyl thiophosphate
O,2,4-dichlorophenyl-O-methylisopropylamido thiophosphate
O,O-diethyl-O,2,5-dichloro-4-bromophenyl thiophosphate
dimethyl-p-(methylthio)-phenylphosphate
O,O-dimethyl-O.p-sulfamidophenyl thiophosphate
O-[p-(p-chlorophenyl)-azophenyl]-O,O-dimethyl thiophosphate
O-ethyl-S-4-chlorophenylethyl dithiophosphonate
O-isobutyl-S-p-chlorophenylethyl dithiophosphonate
O,O-dimethyl-S-p-chlorophenyl thiophosphate
O,O-dimethyl-S-(p-chlorophenylthiomethyl)-dithiophosphate
O,O-diethyl-p-chlorophenylmercaptomethyl dithiophosphate
O,O-diethyl-S-p-chlorophenylthiomethyl thiophosphate
O,O-dimethyl-S-(carbethoxyphenylmethyl)-dithiophosphate
O,O-diethyl-S-(carbofluorethoxyphenylmethyl)-dithiophosphate
O,O-dimethyl-S-(carboisopropoxyphenylmethyl)-dithiophosphate
O,O-diethyl-7-hydroxy-3,4-tetramethylenecoumarinyl thiophosphate
2-methoxy-4-H-1,3,2-benzodioxyphosphorine-2-sulfide
O,O-diethyl-O-(5-phenyl-3-isooxazolyl)-thiophosphate
2-(diethoxyphosphinylimino)-4-methyl-1,3-dithiolane
tris-(2-methyl-1-azirinyl)-phosphine oxide
S-(2-chloro-1-phthalimidoethyl)-O,O-diethyl dithiophosphate
N-hydroxynaphthalimido diethylphosphate
dimethyl-3,5,6-trichloro-2-pyridylphosphate
O,O-dimethyl-O-(3,5,6-trichloro-2-pyridyl)-thiophosphate
S-2-(ethylsulfonyl)-ethyldimethyl thiophosphate
diethyl-S-2-(ethylsulfinyl)-ethyl dithiophosphate
bis-O,O-diethylthiophosphoric anhydride
dimethyl-1,3-di-(carbomethoxy)-1-propen-2-yl phosphate
dimethyl-(2,2,2-trichloro-1-butyrolyoxyethyl)-phosphonate
O,O-dimethyl-O-(2,2-dichloro-1-methoxyvinyl)-phosphate
bis-(dimethylamido)-fluorophosphate
3,4-dichlorobenzyltriphenylphosphonium chloride
dimethyl-N-methoxymethylcarbamoylmethyl dithiophosphate
O,O-diethyl-O-(2,2-dichloro-1-chlorethoxyvinyl)-phosphate
O,O-dimethyl-O-(2,2-dichloro-1-chlorethoxyvinyl)-phosphate
O-ethyl-S,S-diphenyl dithiophosphate
O-ethyl-S-benzylphenyl dithiophosphonate
O,O-diethyl-S-benzyl thiolphosphate
O,O-dimethyl-S-(4-chlorophenylthiomethyl)-dithiophosphate
O,O-dimethyl-S-(ethylthiomethyl)-dithiophosphate
diisopropylaminofluorophosphate
O,O-dimethyl-S-(morpholinylcarbamoylmethyl)dithiophosphate
bis-methylamidophenyl phosphate
O,O-dimethyl-S-(benzenesulfonyl)-dithiophosphate
O,O-dimethyl-(S and O)-ethylsulfinylethyl thiophosphate
O,O-diethyl-O-4-nitrophenylphosphate
triethoxyisopropoxy-bis-(thiophosphinyl)-disulfide
2-methoxy-4H-1,3,2-benzodioxaphosphorine-2-oxide
octamethylpyrophosphoramide
bis-(dimethoxythiophosphinylsulfido)-phenylmethane
N,N-tetramethyldiamidofluorophosphate
O-phenyl-O-p-nitrophenylmethane thiophosphonate
O-methyl-O-(2-chloro-4-tert-butylphenyl)-N-methylamido thiophosphate
O-ethyl-O-(2,4-dichlorophenyl)-phenyl thiophosphate 0,0-diethyl-0-(4-methylmercapto-3,5-dimethyl-
  phenyl)-thiophosphate
4,4'-bis-(0,0-dimethylthiophosphoryloxy)-diphenyl
  disulfide
0,0-di-(β-chloroethyl)-0-(3-chloro-4-methyl-
  coumarinyl-7)-phosphate
S-(1-phthalimidoethyl)-0,0-diethyl dithiophosphate
0,0-dimethyl-0-(3-chloro-4-diethylsulfamylphenyl)-
  thiophosphate
0-methyl-0-(2-carbisopropoxyphenyl)-amido thio-
  phosphate
5-(0,0-dimethylphosphoryl)-6-chlorobicyclo-
  (3,2,0)-heptadiene-(1,5)
0-methyl-0-(2-isopropoxycarbonyl-1-methylvinyl)-
  ethylamido thiophosphate
dichlorodiphenyltrichloroethane
1,1-di-p-chlorophenyl-2,2-dichloroethane
1,1-di-(p-methoxyphenyl)-2,2,2-trichloroethane
1,1-di-(p-ethylphenyl)-2,2-dichloroethane
1,1-di-(p-chlorophenyl)-2,2,2-trichloroethanol
1,1-di-(p-chlorophenyl)-ethanol
ethyl-4,4'-dichlorobenzilate
isopropyl-4,4'-dichlorobenzilate γ-Hexachlorocyclohexane
1,4,5,6,7,8,8-heptachloro-3a-4,7,71-tetrahydro-4,7-
  (endo)-methanoindene
1,2,4,5,6,7,8,8-octachloro-3a, 4,7,7a-tetrahydro-
  4,7(endo)-methanoindane
1,2,3,4,10,10-hexachloro-1,4,4a,5,8,8a-hexahydro-
  1,4-(endo, exo)-5,8-dimethanonaphthalene
1,2,3,4,10,10-hexachloro-6,7-epoxy-1,3,4a,5,6,7,8-
  ,8a-octahydro-1,4-endo, exo)-5,8-dimethanonaphthalene
1,2,3,4,10,10-hexachloro-6,7-epoxy-1,4,4a,5,6,7,8-
  ,8a-octahydro-1,4-(endo, endo)-5,8-dimethanonaphthalene
1,3,4,5,6,7,8,8-octachloro-3a,4,7a-tetrahydro-4,7-
  methanophthalane, 6,7,8,9,10,10-hexachloro-
  1,5,5a,6,9,9a-hexahydro-
6,9-methano-2,4,3-benzodioxathiopine-3-oxide
decachlorooctahydro-1,3,4-methano-2-H-cyclobuta-
  (c,d)-pentalen-2-one
decachloro-bis-(2,4-cyclopentadien-1-yl)
1,2-dibromo-3-chloropropane
Examples of thiol carbamates are:

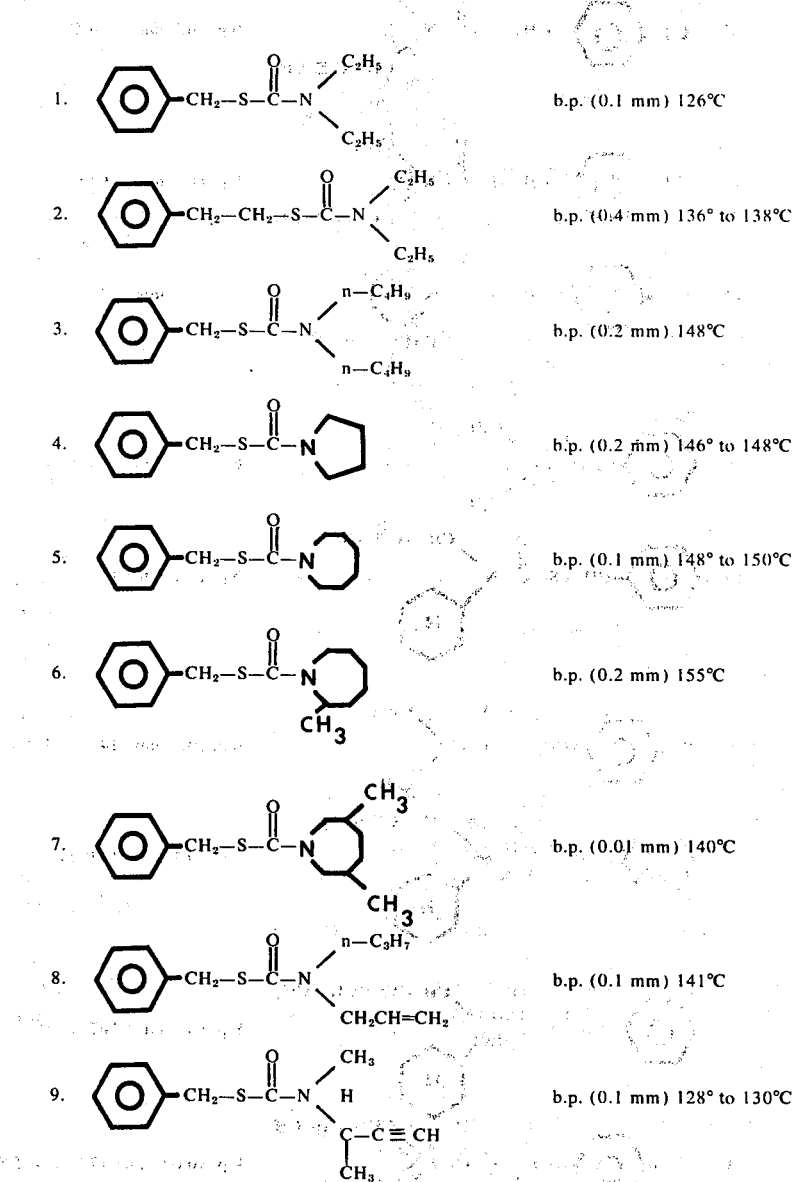

| | | |
|---|---|---|
| 10. | C6H5-CH2-S-C(=O)-N(C2H5)(CH2-C≡CH) | b.p. (0.2 mm) 138° to 140°C |
| 11. | CH3-O-C6H4-CH2-S-C(=O)-N(C2H5)2 | b.p. (0.1 mm) 161° to 163°C |
| 12. | C6H5-CH2-S-C(=O)-N(CH3)2 | b.p. (0.5 mm) 138° to 140°C |
| 13. | Cl-C6H4-CH2-S-C(=O)-N(C2H5)2 | b.p. (0.3 mm) 152°C |
| 14. | Cl-C6H4-CH2-S-C(=O)-N(pyrrolidine) | b.p. (0.4 mm) 186°C |
| 15. | Cl-C6H4-CH2-S-C(=O)-N(CH3)(CH(CH3)-C≡CH) | b.p. (0.2 mm) 156°C |
| 16. | Cl-C6H4-CH2-S-C(=O)-N(C3H7)(CH2-CH=CH2) | b.p. (0.3 mm) 162°C |
| 17. | Cl-C6H4-CH2-S-C(=O)-N(2-methylhexahydroazepine) | b.p. (0.1 mm) 176°C |
| 18. | C6H5-S-C(=O)-N(C2H5)2 | b.p. (0.4 mm) 153° to 155°C |
| 19. | C6H5-CH2-S-C(=O)-N(cyclohexyl)(CH2-C≡CH) | b.p. (0.1 mm) 161°C |
| 20. | CH3-C6H4-CH2-S-C(=O)-N(C2H5)2 | b.p. (0.2 mm) 144° to 145°C |
| 21. | C6H5-CH2-S-C(=O)-N(cyclohexyl)(CH2-CH=CH2) | b.p. (0.3 mm) 163° to 165°C |
| 22. | C6H5-CH2-S-C(=O)-N(cyclohexyl)(CH2-C≡C-CH3) | b.p. (0.3 mm) 167° to 169°C |
| 23. | Cl-C6H4-CH2-S-C(=O)-N(cyclohexyl)(CH2-CH=CH2) | b.p. (0.01 mm) 173° to 175°C |

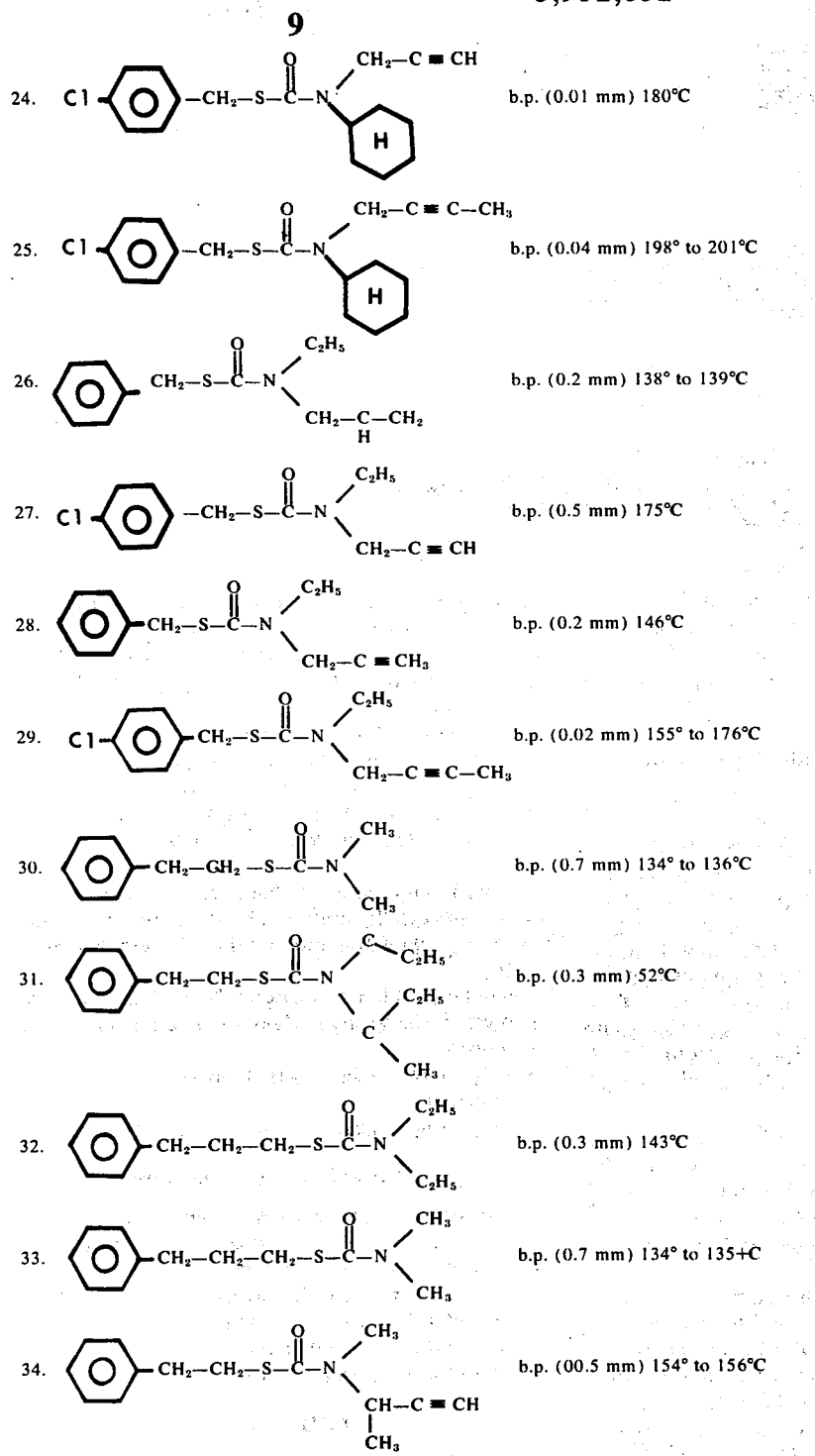
The following processes may be employed for the manufacture of the thiol carbamates:
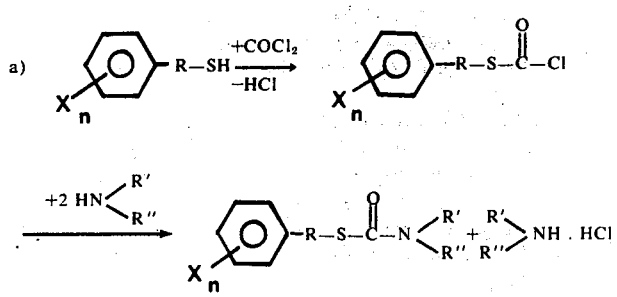

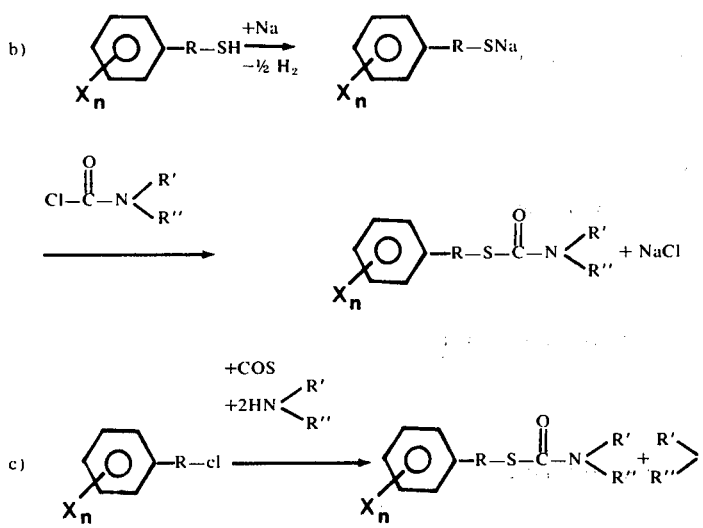

X, N, R, R' and R'' having the above meanings.

The thiol carbamates mentioned above were all prepared by the method designated a) above. The following example demonstrates the procedure employed.

EXAMPLE 1

N-methyl-N-isobutynyl-S-benzylthiol carbamate 373 parts (by weight) of benzylthiol chlorocarbonic ester is placed, together with 800 parts of benzene, in a round flask. At room temperature (20°C) — if necessary, with ice cooling — a solution of 332 parts of N-methyl-N-isobutylamine in 300 parts of benzene is dripped into this solution. The reaction solution is then heated for 2 hours under reflux. The solution is subsequently cooled to room temperature and the amine hydrochloride precipitate filtered off. The filtrate is washed with 400 parts of water and dried with sodium sulfate. The desired product is obtained from the filtrate as a pale yellow oil by distillation under a high vacuum.

Boiling point (0.1 mm): 128° to 130°C.

The agents according to the invention may for instance be used as emulsions, spray powders, dusts or solutions. The ratio of the components to each other is adapted to the prevailing conditions and may vary within wide limits.

To provide as broad a spectrum of insecticidal effectiveness as possible, a further active ingredient selected from the list below may be added as third component to the mixture of thiol carbamate and active ingredient (organophosphorus compound or chlorinated hydrocarbon). The ratio of thiol carbamate to organophosphorus compound or chlorinated hydrocarbon to third component may for example be from 1:0.1 to 10:0.5 to 5, preferably from 1:1:1 to 1:1:5, parts by weight.

Carbamic acid derivatives 1-naphthyl-N-methylcarbamate
2-butynyl-3-chlorophenylcarbamate
4-dimethylamino-3-tolyl-N-methylcarbamate
4-methylthio-3,5-xylyl-N-methylcarbamate
2-chlorophenyl-N-methylcarbamate
1-(dimethylcarbamoyl)-5-methyl-3-pyrazolyl-N,N-dimethylcarbamate
2,3-dihydro-2,2-dimethyl-7-benzofuranyl-N-methylcarbamate
2-methyl-2-methylthiopropionaldehyde-0-(methylcarbamoyl)-oxime
8-quinaldyl-N-methylcarbamate and its salts
3-isopropyl-5-methylphenyl-N-methylcarbamate
2-(1,3-dioxolan-2-yl)-phenyl-N-methylcarbamate
2-(4,5-dimethyl-1,3-dioxolan-2-yl)-phenyl-N-methylcarbamate
2-(1,3-dithiolan-2-yl)-phenyl-N-methylcarbamate
2-(1,3-dithiolan-2-yl)-phenyl-N,N-dimethylcarbamate
2-isopropoxyphenyl-N-methylcarbamate
4-diallylamino-3,5-xylyl-N-methylcarbamate
1-isopropyl-3-methylpyrazol-5-yl-N,N-dimethylcarbamate
1-methylthioethylimino-N-methylcarbamate
2-(propargylethylamino)-phenyl-N-methylcarbamate
2-(propargylmethylamino)-phenyl-N-methylcarbamate
2-(dipropargylamino)-phenyl-N-methylcarbamate
3-methyl-4-(dipropargylamino)-phenyl-N-methylcarbamate
3,5-dimethyl-4-(dipropargylamino)-phenyl-N-methylcarbamate
2-(allylisopropylamino)-phenyl-N-methylcarbamate.

Nitrophenols and derivatives 4,6-dinitro-6-methylphenol, sodium salt
dinitrobutylphenol (2,2',2'''-triethanolamine salt)
2-cyclohexyl-4,6-dinitrophenol
2-(1-methylheptyl)-4,6-dinitrophenyl crotonate
2-sec-butyl-4,6-dinitrophenyl-3-methyl butenoate
2-sec-butyl-4,6-dinitrophenyl cyclopropionate
2-sec-butyl-4,6-dinitrophenyl isopropyl carbonate

Miscellaneous pyrethrin I
pyrethrin II
3-allyl-2-methyl-4-oxo-2-cyclopenten-1-yl chrysanthemumate
6-chloripernoyl chrysanthemumate
2,4-dimethylbenzyl chrysanthemumate
2,3,4,5-tetrahydrophthalimidomethyl chrysanthemumate
4-chlorobenzyl-4-chlorophenyl sulfide
6-methyl-2-oxo-1,3-dithiolo-[4,5-b]-quinoxaline
(1)-3-(2-furfuryl)-2-methyl-4-oxocyclopent-2-enyl-(1)-(cis + trans)-chrysanthemum monocarboxylate
2-pivaloyl-indane-1,3-dione
N'-(4-chloro-2-methylphenyl)-N,N-dimethylformamidine
4-chlorobenzyl-4-fluorophenyl sulfide 5,6-dichloro-1-phenoxycarbanyl-2-trifluoromethyl benzimidazole
p-chlorophenyl-p-chlorobenzene sulfonate
p-chlorophenyl benzene sulfonate
p-chlorophenyl-2,4,5-trichlorophenyl sulfone
p-chlorophenyl-2,4,5-trichlorophenyl sulfide
p-chlorobenzyl-p-chlorophenyl sulfide
2-thio-1,3-dithiolo-(5,6)-quinoxaline
prop-2-ynyl-(4-t-butylphenoxy)-cyclohexyl sulfite.

The following examples demonstrate the action of some of the agents according to the invention. The thiol carbamates are numbered as in the table above.

EXAMPLE 2

Bran bugs (Tribolium confusum) which have developed a high degree of resistance to 0,0-dimethyl-S-(1,2-dicarbethoxy)-ethyl dithiophosphate (I) are placed on circular filter papers (7 cm in diameter) which have been treated with acetonic solutions of the active ingredients. The kill rate is determined after 24 hours.

| Active ingredient | Amount of active ingredient in mg/filter paper | Effectiveness |
|---|---|---|
| 1 | 5 | ineffective |
| I+2 | 0.25 + 0.25 | 100% mortality |
| I+9 | 0.25 + 0.25 | 100% mortality |
| I+3 | 0.25 + 0.25 | 100% mortality |
| I+8 | 0.25 + 0.25 | 100% mortality |
| 2 | 5 | ineffective |
| 9 | 5 | ineffective |
| 3 | 5 | ineffective |
| 8 | 5 | ineffective |
| I+13 | 0.5 + 0.5 | 100% mortality |
| 13 | 5 | ineffective |

EXAMPLE 3

Animals from a strain of the croton bug (Blattella germanica) having marked resistance to insecticides from the group of organophosphorus compounds are treated as follows:

The insides of 1 liter glass beakers are wetted with acetonic solutions of the active ingredients. After the solvent has evaporated, 10 adult bugs are placed in each beaker. The action is determined after 48 hours.

| Active ingredient | Amount of active ingredient mg/breaker | Effectiveness |
|---|---|---|
| 1 | 0.4 | 30% mortality |
| I+2 | 0.02 + 0.02 | 100% mortality |
| I+9 | 0.1 + 0.1 | 100% mortality |
| I+3 | 0.1 + 0.1 | 100% mortality |
| I+8 | 0.04 + 0.04 | 100% mortality |
| 2 | 0.4 | ineffective |
| 9 | 0.4 | ineffective |
| 3 | 0.4 | ineffective |
| 8 | 0.4 | ineffective |
| I+13 | 0.01 + 0.01 | 90% mortality |
| 13 | 0.4 | ineffective |

We claim:

1. An insecticide composition comprising an insecticidally effective amount of a mixture (a) 0,0-dimethyl-S-(1,2-dicarbethoxy)-ethyl dithiophosphate and (b) a member selected from the group consisting of

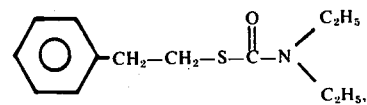

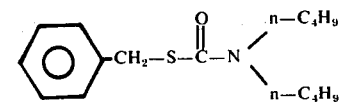

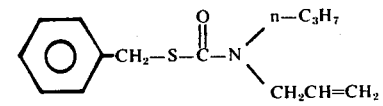

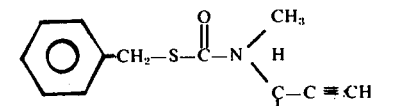

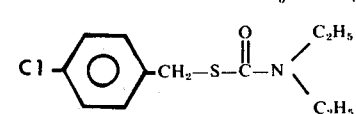

in a weight ratio of 1:1.

2. An insecticide composition comprising an insecticidally effective amount of a mixture (a) 0,0-dimethyl-S-(1,2-dicarbethoxy)-ethyl dithiophosphate and (b) S-ethylphenyl-N-diethyl thiolcarbamate in a weight ratio of 1:1.

3. A process for killing insects which comprises contacting the insects with an insecticidally effective amount of a mixture of (a) 0-0-dimethyl-S-(1,2-dicorbethoxy)-ethyl dithiophosphate and (b) a member selected from the group consisting of

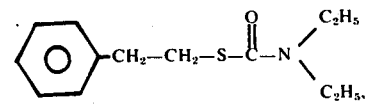

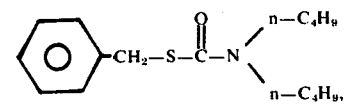

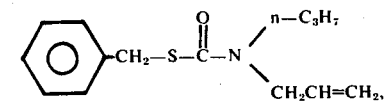

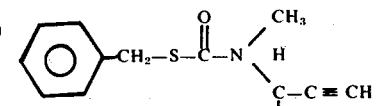

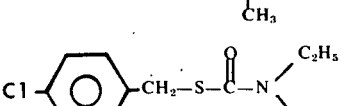

in a weight ratio of 1:1.

4. A process for killing insects which comprises contacting the insects with an insecticidally effective amount of a mixture of (a) 0,0-dimethyl-S-(1, 2-dicarbethoxy)-ethyl dithiophosphate and (b) S-ethylphenyl-N-diethyl thiocarbamate in a weight ratio of 1:1.

* * * * *

UNITED STATES PATENT AND TRADEMARK OFFICE
CERTIFICATE OF CORRECTION

PATENT NO. : 3,932,632
DATED : January 13, 1976
INVENTOR(S) : ADOLPHI et al

It is certified that error appears in the above-identified patent and that said Letters Patent are hereby corrected as shown below:

In Column 6, Line 4, delete "... 4,7,7,a-tetrahydro- ..."
and substitute --... 4,7,7a-tetrahydro- ...--

In Column 7 and 8, Example 13, delete " b.p. (0.3 mm) 1520°C "
and substitute -- b.p. (0.3 mm) 152°C --

In Column 7 and 8, Example 22, a triple bond should join the "C" to the "CH"

In Column 9 and 10, Example 27, delete " b.p. (0.5 mm) 175°C "
and substitute -- b.p. (1.5 mm) 175°C --

In Column 9 and 10, Example 29, delete " b.p. (0.02 mm) 155° to 176°C " and substitute -- b.p. (0.02 mm) 155° to 170°C --

In Column 9 and 10, Example 33, delete " b.p. (0.7 mm) 134° to 135+C " and substitute -- b.p. (0.7 mm) 134° to 135°C --

In Column 11, Line 25, delete "... demonstrates ghe ..."
and substitute --... demonstrates the ...--

In Column 11, formula "c", delete "  "

and substitute
-- 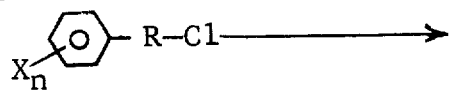 --

Signed and Sealed this
Thirtieth Day of November 1976

[SEAL]

Attest:

RUTH C. MASON
*Attesting Officer*

C. MARSHALL DANN
*Commissioner of Patents and Trademarks*